United States Patent [19]

Esanu

[11] Patent Number: 4,720,487
[45] Date of Patent: Jan. 19, 1988

[54] BORNANE DERIVATIVES, THEIR PREPARATION AND THERAPEUTIC COMPOSITIONS CONTAINING THE SAME

[75] Inventor: André Esanu, Paris, France

[73] Assignee: Societe de Conseils de Recherches et d'Applications Scientifiques (S.C.R.A.S.), Paris, France

[21] Appl. No.: 718,065

[22] Filed: Apr. 1, 1985

[30] Foreign Application Priority Data

Apr. 24, 1984 [GB] United Kingdom ................ 8410484

[51] Int. Cl.$^4$ ............................................. A61K 31/70
[52] U.S. Cl. ........................................ 514/43; 514/46; 514/48; 514/52; 514/821; 514/824; 536/23; 536/24; 536/26; 536/28; 536/29
[58] Field of Search ...................... 536/23, 24, 26, 28, 536/29; 514/43, 46, 48, 52, 824, 821

[56] References Cited

U.S. PATENT DOCUMENTS 3,868,361  2/1975  Tolman et al. ................... 536/28
4,590,180  5/1986  Irmscher et al. ................ 536/26

Primary Examiner—J. R. Brown
Assistant Examiner—John W. Rollins, Jr.
Attorney, Agent, or Firm—Lucas & Just

[57] ABSTRACT

This invention relates to bornane derivatives of the formula:

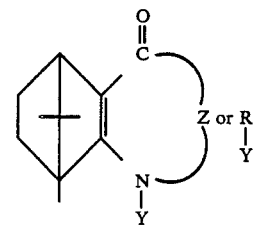

wherein Z stands for:

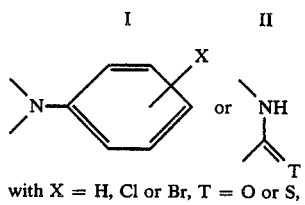

with X = H, Cl or Br, T = O or S, and Y stands for an arabinose, xylose or ribose rest, the acetylated form of the same, with either a pyrane or furane configuration and bound to the R rest to lead either to the $\alpha$ or to the $\beta$ anomer, to a process for the preparation of these compounds and to therapeutic compositions comprising one of them as an essential ingredient.

2 Claims, No Drawings

BORNANE DERIVATIVES, THEIR PREPARATION AND THERAPEUTIC COMPOSITIONS CONTAINING THE SAME

The present invention relates to new bornane derivatives of the formula:

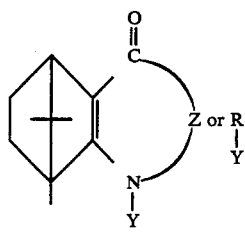

wherein Z stands for:

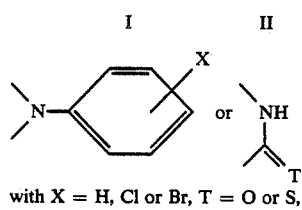

with X = H, Cl or Br, T = O or S, and Y stands for an arabinose, xylose or ribose moiety, the acetylated form of the same, with either a pyranose or furanose configuration and bound to the R moiety of either the α or the β anomer.

These compounds are more particularly interesting for their therapeutic action in the field of virus- and bacteria-induced diseases and, for some of them, for their activity of the cardio-vascular field.

The invention relates also to a process for the preparation of these compounds consisting in reacting, in acetonitrile, at room temperature and under nitrogen circulation, stoichiometric proportions of the compond R—H and of the selected ose, under its acetylated form, in the presence of 1,1,1,3,3,3-hexamethyldisilazane, trimethylchlorosilane and tin tetrachloride; the reaction is performed under stirring for 12 to 24 hours.

This leads to the acetylated form of the compounds of the invention; the corresponding non-acetylated compounds are obtained by the usual desacetylation techniques.

The invention relates finally to a therapeutic composition of matter comprising, as an essential ingredient therein, an effective amount of a compound of claim 1, associated with an appropriate carrier.

As to the starting material:

A—The acetylated oses are obtained from the corresponding oses, by acetylation, as usual, by an excess of acetic anhydride in the presence of perchloric acid, under stirring at room temperature (0.5 to one hour). The reaction mixture is poured on icy water, which gives an oily product, extracted by chloroform and dried. The evaporation of chloroform under reduced pressure leads to an oil with a yield of about 55 to 85% according to the product. As these oses exist under pyranose and furanose form, each of these forms or their mixtures in various proportions may be used.

B—The various condensed ring RH are obtained as follows:

(a) Z is I: RH=a

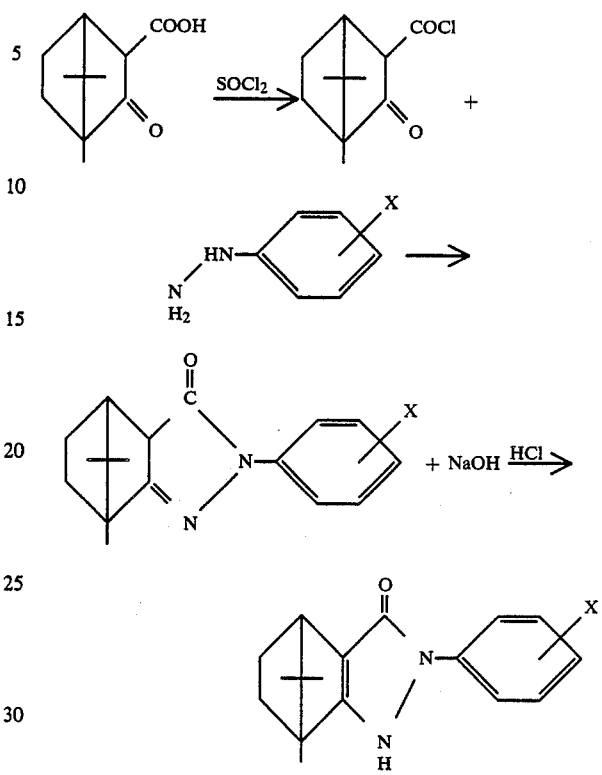

The reaction is described with X=H and performs similarly when X is the selected substituent. In a one liter reactor are poured 196 g (1 mol) of camphocarbonic acid and 95 ml (1.25 mol) of SOCl₂; the mixture is stirred overnight at room temperature. After elimination of non-reacted SOCl₂, the resulting product is treated by benzene then by petroleum ether, which is evaporated under reduced pressure; there is obtained an oily product which is refluxed 4 hours in a 6 liter reactor with 3.5 l of benzene and 119 g (1.1 mol) of phenylhydrazine. After stirring overnight and elimination of a small insoluble fraction by filtration, the mixture is concentrated to dryness, which gives a crystalline product recrystallyzed in petroleum ether. Yield 267.5 g (93%) of an amide which is treated by 72 g (1.8 mol) of NaOH and 1.5 l of water in a 4 liter reactor at reflux. After cooling (ice bath) and acidification (HCl), there is obtained a precipitate, which is washed and dried. Yield 206.5 g (85%).

(b) Z is II: RH=b

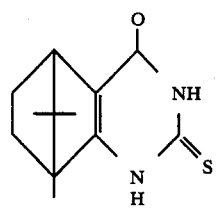

The reaction is performed as above except that phenylhydrazine is replaced by thiourea (80 g or 1.05 mol) which leads to 230 g (yield 90%) of intermediate product and 173 g (yield 82%) of final product. Urea is used for T=O.

Accordingly, the starting material RH is:

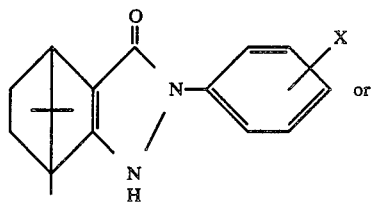

(a)

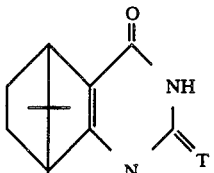

(b)

with X=H, Cl or Br, T=S or O.

The invention will be better understood from the following examples. As the process is strictly the same for all the compounds, only the first example will be described in details; for the other examples, only starting materials and characteristics will be given.

Example A: RH=a (1)

N-1-(β-D-2,3,4-tri-O-acetylribopyranosyl)-2-phenyl-4,5,6,7-tetrahydro-7,8,8-trimethyl-4,7-methano-indazole-3-one.

X=H   β-D-ribopyranose

In a one liter reactor fitted with stirring means are poured, under nitrogen circulation, 21.4 g (0.08 mol) of 2-phenyl-4,5,6,7-tetrahydro-7,8,8-trimethyl-4,7-methanoindazole-3-one, 12.3 ml (0.0585 mol) of hexamethyldisilazane, 27.3 ml (0.0215 mol) of tetramethylchlorosilane, 18.7 ml (0.16 mol) of SnCl₄ and 250 ml of acetonitrile; after stirring, there is obtained a solution to which are added 25.5 g (0.08 mol) of β-D-tetraacetylribopyranose. Stirring is maintained for 24 hours under nitrogen circulation. The reacting mixture is then poured on a cold 10% NaHCO₃ solution and pH is adjusted to 6.7; 300 ml of CHCl₃ are added under stirring and the organic phase is separated, washed with water, dried by sodium sulfate and evaporated to dryness. The dry product is then triturated with diethyl ether and recrystallized by hot ethanol. After separation, washing and drying, there is obtained 13 g (yield 31%) of a white crystalline product, the analysis of which shows a perfect correspondence with the formula $C_{28}H_{34}N_2O_8$. Melting point 191° C. (Tottoli). This compound is insoluble in water and dimethylsulfoxide.

The corresponding desacetylated product (formula $C_{22}H_{28}N_2O_5$) is a white crystalline product melting at 175°–177° C. (Tottoli) and soluble in water and dimethylsulfoxide.

(2)

N-1-(β-D-2,3,5-tri-O-acetylribofuranosyl)-2-phenyl-4,5,6,7-tetrahydro-7,8,8-trimethyl-4,7-methano-indazole-3-one.

X=H   β-D-ribofuranose

Reaction time 19 hours—Yield 29.5% of a white crystalline product melting at 135° C. (Tottoli). Insoluble in water, soluble in dimethylsulfoxide. Analysis shows a perfect correspondence with the formula $C_{28}H_{34}N_2O_8$.

The corresponding desacetylated product (formula $C_{22}H_{28}N_2O_5$) is a beige powder melting at 230°–231° C. (Tottoli), insoluble in water and soluble in dimethylsulfoxide.

(3)

N-1-(β-D-2,3,5-tri-O-acetyl-ribofuranosyl)-2-p-chlorophenyl-4,5,6,7-tetrahydro-7,8,8-trimethyl-4,7-methano-indazole-3-one.

X=Cl   β-D-ribofuranose

Reaction time 13 hours—yield 33% of a white crystalline product melting at 178° C. (Tottoli). Insoluble in water and in dimethylsulfoxide. Analysis shows a good correspondence with the formula $C_{28}H_{33}N_2O_8Cl$.

The corresponding desacetylated product (formula $C_{22}H_{27}N_2O_5Cl$) is a beige crystalline product melting at 187°–189° C. (Tottoli), insoluble in water and in dimethylsulfoxide.

(4)

N-1-(D-2,3,5-tri-O-acetylarabinopyranosyl)-2-phenyl-4,5,6,7-tetrahydro-7,8,8-trimethyl-4,7-methano-indazole-3-one.

X=H   D-arabinopyranose

Reaction time 17 hours—Yield 37% of a white crystalline product melting at 167° C. (Tottoli). Insoluble in water, soluble in dimethylsulfoxide. Analysis shows a perfect correspondence with the formula $C_{28}H_{34}N_2O_8$.

The corresponding desacetylated product (formula $C_{22}H_{28}N_2O_5$) is a white powder melting at 183°–185° C. (Tottoli), insoluble in water and soluble in dimethylsulfoxide.

Example B: RH=b (1)

N-1-(β-D-2,3,4-tri-O-acetylribopyranosyl)-5,6,7,8-tetrahydro-8,9,9-trimethyl-5,8-methanoquinazoline-2-thioxo-4-one.

T=S   β-D-ribopyranose

Reaction time 22 hours—Yield 30.5% of a white crystalline product melting at 170° C. (Tottoli), with decomposition. Insoluble in water, soluble in dimethylsulfoxide. Analysis shows a perfect correspondence with the formula $C_{23}H_{30}N_2O_8S$.

The corresponding desacetylated product (formula $C_{17}H_{24}N_2O_5S$) is a white product melting at 217° C. (Tottoli), soluble in water and in dimethylsulfoxide.

(2)

N-1-(β-D-2,3,5-tri-O-acetylribofuranosyl)-5,6,7,8-tetrahydro-8,9,9-trimethyl-5,8-methanoquinazoline-2-thioxo-4-one.

T=S   β-D-ribofuranose

Reaction time 20 hours—Yield 28% of a white crystalline product melting at 148° C. (Tottoli), with decomposition. Insoluble in water, soluble in dimethylsulfoxide. Analysis shows a perfect correspondence with the formula $C_{23}H_{30}N_2O_8S$.

The corresponding desacetylated product (formula $C_{17}H_{24}N_2O_5S$) is a white product melting at 227° C. (Tottoli). Soluble in water and in dimethylsulfoxide.

(3)
N-1-(D-2,3,4-tri-O-acetylarabinopyranose)-5,6,7,8-tetrahydro-8,9,9-trimethyl-5,8-methanoquinazoline-2-thioxo-4-one.

T=S   α+β arabinopyranose

Reaction time 16 hours—Yield 26% of a white powder melting at 127° C. (Tottoli). Insoluble in water, soluble in dimethylsulfoxide. Analysis shows a perfect correspondence with the formula $C_{23}H_{30}N_2O_8S$.

The corresponding desacetylated product (formula $C_{17}H_{24}N_2O_5S$) is a white product melting at 204° C. (Tottoli). Soluble in water and in dimethylsulfoxide.

(4)
N-1-(D-2,3,5-tri-O-acetylarabinofuranose)-5,6,7,8-tetrahydro-8,9,9-trimethyl-5,8-methanoquinazoline-2-thioxo-4-one.

T=S   α+β furanose

Reaction time 17 hours—Yield 26% of a white crystalline powder melting at 127° C. (Tottoli). Insoluble in water, soluble in dimethylsulfoxide. Analysis shows a perfect correspondence with the formula $C_{23}H_{30}N_2O_8S$.

The corresponding desacetylated product (formula $C_{17}H_{24}N_2O_5S$) is a white product melting at 193° C. (Tottoli). Insoluble in water, soluble in dimethylsulfoxide.

(5)
N-1-(β-D-2,3,4-tri-O-acetylribopyranosyl)-5,6,7,8-tetrahydro-8,9,9-trimethyl-5,8-methanoquinazoline-2,4-dione.

T=O   β-D-ribopyranose

Reaction time 21 hours—Yield 28.5% of a white crystalline powder melting at 181° C. (Tottoli). Insoluble in water, soluble in dimethylsulfoxide. Analysis shows a perfect correspondence with the formula $C_{23}H_{30}N_2O_9$.

The corresponding desacetylated product (formula $C_{17}H_{24}N_2O_6$) is a white product melting at 212° C. (Tottoli). Soluble in water and in dimethylsulfoxide.

(6)
N-1-(β-D-2,3,4-tri-O-acetylribofuranosyl)-5,6,7,8-tetrahydro-8,9,9-trimethyl-5,8-methanoquinazoline-2,4-dione.

T=O   β-D-ribofuranose

Reaction time 18 hours—Yield 31.5% of a white crystalline product at 196° C. (Tottoli). Insoluble in water, soluble in dimethylsulfoxide. Analysis shows a perfect correspondence with the formula $C_{23}H_{30}N_2O_9$.

The corresponding desacetylated product (formula $C_{17}H_{24}N_2O_6$) is a white product melting at 166° C. (Tottoli). Soluble in water and in dimethylsulfoxide.

TOXICITY

Preliminary toxicity studies per os on rats and mice have not revealed any toxicity at 600 mg/kg for any of the compounds. As maximum efficient therapeutic doses are of about 50 mg/kg, slightly varying with the compounds, higher doses have not been tested.

PHARMACOLOGY

The activity of the compounds of the invention was researched in an in vivo protection test of mice infected intravaginally with Herpes Simplex Type II virus. Mice were infected and treated according to the method described by A. K. Field, M. E. Davies et al. (Proc. Natl. Acad. Sci., 80, 4139; 1983) slightly modified. Female $CD_1$ mice were divided in groups of ten except for the negative controls which housed 20 mice. After a quarantine period of two weeks, each group of mice were vaginally swabbed with saline, and a tampon saturated with undiluted Herpes Simplex Type II virus was inserted in the vagina. One hour after tampon insertion, each group of ten animals was administered per os with 0.1 ml of the appropriate test substance suspended in methylcellulose. Several hours later, mice were again administered with test substances orally. On the second day, tampons were removed and replaced by newly Herpes Simplex Type II virus-soaked tampons. Mice were also administered twice orally with test substances. On the third day, tampons were definitely removed, and oral administration of the test compounds were repeated twice daily for 10 days. Animals were observed for mortality for 21 days. Detailed results for each compound are shown in the following table. Acyclovir was used as reference compound and administered orally twice a day for 10 days at 50 mg/kg as for the tested compounds. The compounds are identified by the number of their example as such for the acetylated form or followed by (OH) for the desacetylated form. In each Day column, I stands for % of mortality and II for % of protection.

The in vitro antiviral activity of the compounds of the invention was also assessed by the plaque reduction test against both HSV-1 and HSV-2 viruses. Each of the synthetized compounds was tested at concentrations of 0.0125 μg/ml–10 μg/ml dissolved in tissue culture medium containing 0.2% carboxymethyl cellulose (CMC) and 0.2% tween 80. Generally, a plateau effect was observed for each compound for concentrations of 0.5–10 μg/ml; at lower concentrations plaque inhibition was reduced. Similar results were contained against HSV-2 where a plateau effect was observed at concentrations between 1 and 10 μg/ml., but below this concentration the plaque reduction was reduced. From these results, maximum activity of the compounds was demonstrable but at concentrations of about 0.5 μg/ml against HSV-1 virus and between 0.5 and 1.0 μg/ml against HSV-2 virus: at higher concentrations the compounds were probably not further absorbed, and at lower concentrations the compounds had less antiviral activity.

PRESENTATION - POSOLOGY

The compounds of the invention may be presented in tablets or gelatine capsules for oral administration in dose units containing 100 mg of active ingredient, associated with an appropriate carrier. Posology, per os, in human therapy is from 1 to 8 dose units per diem.

Preparations for topical applications include gels, lotions and sprays containing 1 to 5% in weight of active ingredient, dissolved in diethyleneglycol monoethyl ether.

TABLE

| COMPOUND | DAY 10 I | DAY 10 II | DAY 16 I | DAY 16 II | DAY 21 I | DAY 21 II |
|---|---|---|---|---|---|---|
| Control | 10 | — | 40 | — | 45 | — |
| Acyclovir | 20 | 0 | 26 | 35 | 27 | 40 |
| A₁(OH) | 10 | 0 | 30 | 25 | 30 | 33 |
| A₁ | 0 | 100 | 20 | 50 | 20 | 56 |
| A₂ | 0 | 100 | 10 | 75 | 10 | 78 |
| A₂(OH) | 10 | 0 | 20 | 50 | 20 | 56 |
| A₄ | 0 | 100 | 20 | 50 | 20 | 56 |

TABLE-continued

| COMPOUND | DAY 10 I | DAY 10 II | DAY 16 I | DAY 16 II | DAY 21 I | DAY 21 II |
|---|---|---|---|---|---|---|
| $B_1$ | 0 | 100 | 10 | 75 | 10 | 78 |
| $B_3$ | 0 | 100 | 10 | 75 | 10 | 78 |
| $B_4$ | 10 | 0 | 10 | 75 | 10 | 78 |

I claim:

1. Bornane derivatives of the formula:

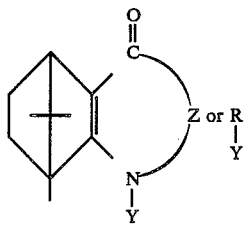

wherein Z stands for:

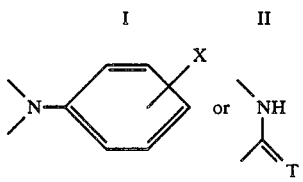

with X = H, Cl or Br, T = O or S, and y stands for an arabinose, xylose or ribose moiety, the acetylated form of the same, with either a pyranose or furanose configuration and bound to the R moiety of either the $\alpha$ or the $\beta$ anomer.

2. A therapeutic composition comprising an effective amount, said effective amount being selected from the group consisting of an antivirally effective amount, an antibacterially effective amount, and a cardiovascularly effective amount, of a compound according to claim 1 in a pharmaceutically acceptable carrier.

* * * * *

UNITED STATES PATENT AND TRADEMARK OFFICE
CERTIFICATE OF CORRECTION

PATENT NO. : 4,720,487
DATED : January 19, 1988
INVENTOR(S) : Andre Esanu

It is certified that error appears in the above–identified patent and that said Letters Patent are hereby corrected as shown below:

In the Abstract, lines 5 and 6, delete "pyrane or furane" and substitute therefor --pyranose or furanose--; lines 6 and 7, delete "rest to lead either to the α or to" and substitute therefor --moiety of either the α or--.

Column 1, line 41, change "compond" to --compound--.

The first formula of the Abstract, the formula at column 1, lines 7-18, and the formula at column 7, lines 12-21 should all be deleted and the following formula substituted therefor:

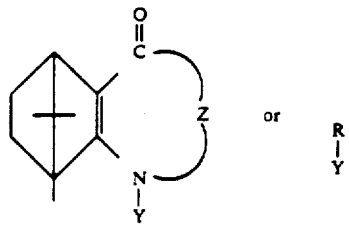

Signed and Sealed this

Twenty-second Day of November, 1988

Attest:

DONALD J. QUIGG

Attesting Officer

Commissioner of Patents and Trademarks